| 
US009322769B2

(12) United States Patent
Alfano et al.

(10) Patent No.: US 9,322,769 B2
(45) Date of Patent: Apr. 26, 2016

(54) METHOD AND APPARATUS FOR DETECTING DEGREE OF SPOILAGE OF FOOD

(71) Applicants: Robert R. Alfano, New York, NY (US); Yang Pu, New York, NY (US); Wubao Wang, Flushing, NY (US)

(72) Inventors: Robert R. Alfano, New York, NY (US); Yang Pu, New York, NY (US); Wubao Wang, Flushing, NY (US)

( * ) Notice: Subject to any disclaimer, the term of this patent is extended or adjusted under 35 U.S.C. 154(b) by 0 days.

(21) Appl. No.: 14/309,598

(22) Filed: Jun. 19, 2014

(65) Prior Publication Data

US 2014/0300891 A1     Oct. 9, 2014

Related U.S. Application Data

(63) Continuation-in-part of application No. PCT/US2012/070235, filed on Dec. 18, 2012.

(51) Int. Cl.
*G01J 3/00*      (2006.01)
*G01N 21/27*   (2006.01)
*G01N 33/12*   (2006.01)
*G01N 21/64*   (2006.01)

(52) U.S. Cl.
CPC ............ *G01N 21/27* (2013.01); *G01N 21/6486* (2013.01); *G01N 33/12* (2013.01)

(58) Field of Classification Search
CPC . G01N 21/314; G01N 21/33; G01N 21/3504; G01J 3/10; G01J 3/42
USPC .......................................................... 356/51
See application file for complete search history.

(56) References Cited

U.S. PATENT DOCUMENTS

| | | | | |
|---|---|---|---|---|
| 2002/0119513 A1* | 8/2002 | Alocilja et al. | ................. | 435/34 |
| 2003/0160182 A1* | 8/2003 | Petrich et al. | .............. | 250/458.1 |
| 2004/0248285 A1* | 12/2004 | Casey et al. | ................. | 435/287.2 |
| 2005/0284172 A1* | 12/2005 | Walker et al. | ................... | 62/458 |
| 2006/0078058 A1* | 4/2006 | Lin | .............................. | 375/260 |
| 2008/0058649 A1* | 3/2008 | Boyden et al. | ................ | 600/476 |
| 2010/0088038 A1* | 4/2010 | Almiman | ........................ | 702/22 |
| 2010/0332333 A1* | 12/2010 | Neff | ............................... | 705/15 |

* cited by examiner

*Primary Examiner* — Tarifur Chowdhury
*Assistant Examiner* — Md M Rahman
(74) *Attorney, Agent, or Firm* — Myron Greenspan Lackenbach Siegel LLP (57) ABSTRACT

A method detects the degree of spoilage of food by exposing a food sample to an excitation wave having a first wavelength of about 340 nm or about 380 nm, wherein the excitation wave has a bandwidth of 40 nm or less. The excitation wave is permitted to interact with the food sample and return emission spectra. A detector detects the emission spectra. A predetermined threshold value is established which defines when a food sample is or is not spoiled. The emission spectra is analyzed at a second wavelength of about 400 nm, about 450 nm or about 530 nm to provide a test or measured value of the emission spectra indicative of the degree of spoilage of the food sample. Whether or not a food sample is spoiled beyond the predetermined threshold is determined by comparing the measured value to the predetermined threshold value.

16 Claims, 12 Drawing Sheets

METHOD AND APPARATUS FOR DETECTING DEGREE OF SPOILAGE OF FOOD

CROSS-REFERENCE TO RELATED APPLICATIONS

This application claims priority to and the benefit of U.S. provisional patent application Ser. No. 61/630,766, filed Dec. 19, 2011, which is incorporated herein by reference in its entirety and is a continuation-in-part of PCT International Patent Application No. PCT/US2012/070235 having an International Filing date of Dec. 18, 2012.

BACKGROUND OF THE INVENTION

1. Field of the Invention

This invention relates, in one embodiment, to a spectroscopic method and apparatus for detecting the degree of food spoilage of a food sample.

2. Description of the Prior Art

Over the past several decades, concerns have been raised on food safety due to the addition and generation of pathogen within the meat and other kinds of food for public consumption and health. These concerns, along with concerns over specific pathogenic bacteria within meats (namely *Salmonella* spp., *E. coli* 0157:117, and *Campylobacter* spp.) have focused attention on the requirement for a rapid (less than a few minutes) and accurate detection techniques for microbiologically spoiled or contaminated meat. There are a limited number of conventional methods proposed to detect spoilage in muscle foods. These method are time-consuming and labor-intensive, and give retrospective information.

Therefore, an improved method for detecting spoilage of food is desired.

SUMMARY OF THE INVENTION

This disclosure is directed to methods and systems for detecting spoilage of food items including pork, chicken, beef, veal, fish, rice food and wheat food (e.g. bread). Specific excitation wavelengths are selected that interact with key fluorophores related to food spoilage. These fluorophores include collagen, NADH and flavin. The disclosed method uses native fluorescence spectroscopy, which is fast, easy and is a no-contact-method. The system for implementing the method may be small, light weight, low cost and permits real-time monitoring of food spoilage but the system can also be incorporated into residential, commercial and/or industrial food processing, storage or refrigeration units.

An advantage that may be realized in the practice of some disclosed embodiments of the Method is the ability to detect food spoilage, in real-time, without the use of chemical additives or otherwise contacting the food.

BRIEF DESCRIPTION OF THE DRAWINGS

The present invention is disclosed with reference to the accompanying drawings, wherein:

FIG. 2A and FIG. 2B are absorption spectra of collagen, NADH and flavin, and several other known fluorophores in muscle tissue, while

FIGS. 6A and 6B are fluorescence spectra of white rice stored at room temperature measured at hour 0 (FIG. 6A) and hour 12 (FIG. 6B) while

Corresponding reference characters indicate corresponding parts throughout the several views. The examples set out herein illustrate several embodiments of the invention but should not be construed as limiting the scope of the invention in any manner.

DETAILED DESCRIPTION

Disclosed in this specification is a spectroscopic method and system for detecting the degree of spoilage of food. A specific excitation wavelength is utilized to detect the degree of spoilage of food without adding extra reagents or contacting the food. The specific excitation wavelength(s) are selected to interact with one or more principle fluorophores that are related to food spoilage. These principle fluorophores include collagen, nicotinamide adenine dinucleotide plus hydrogen (NADH) and flavin. In response to the specific excitation wavelength(s), each fluorophore returns a characteristic emission spectra which may be analyzed to determine the concentration of the particular fluorophore. These concentrations are correlated with degree of food spoilage.

Food consists to a large extent of cells from plants or animals and biological material with this origin (juice, fat and starch etc). Although food spoilage is not exclusively a result of microbial degradation (other spoilage reactions include dehydration, oxidation of fat and endogenous metabolism, etc.) microbial degradation is one of the more important types of reaction for food spoilage. Most foods have a primary flora of microorganisms (e.g. bacteria) which originates from the production environment. During food processing, the additional contaminants (e.g. secondary flora) from the air, water, equipment, or handlers infects the food. When the number of microorganisms exceeds 10 to 10 microorganisms per square centimeter, the food usually develops bad smell and the microflora is then referred to as spoilage flora.

Meat is normally contaminated by an aerobic psychrotrophic flora dominated by *Pseudomonas* spp. The degradation of meat is mainly catalyzed by these microorganisms which collectively carry an enormously diverse range of metabolic capacities. These metabolic capacities include respiration functions for the generation of energy.

All energy is generated, with exception of photosynthesis, by oxidation of reduced carbon compounds, e.g. sugars. When oxygen is used as the ultimate oxidant, it is called aerobic respiration. The use of alternative oxidant, like nitrate, etc., is called anaerobic respiration. Aerobic respiration and nitrate respiration are mainly responsible for food spoilage. Aerobic respiration involves glycolysis and the tricarboxylic acid cycle (Krebs cycle). Glycolysis is the most common pathway in bacteria for sugar catabolism, which can be divided into stages, the last of which is characterized by a net gain of the energy-rich molecules ATP and NADH. Since the concentration of NADH increases during bacterial growth in the meat, the change of the fluorescence intensity of NADH may be used as a fingerprint to evaluate spoilage of the meat.

In the exemplary embodiments described herein, Multivariate Curve Resolution with Alternating Least-Squares (MCR-ALS) is used. The native fluorescence spectra, combined with MCR-ALS analysis, were used to directly monitor changes of the principle fluorophore concentrations in the meat to produce biochemically interpretable "fingerprints" for food spoilage. These fingerprints reflect the microbial spoilage of muscle foods (e.g. pork, chicken, beef, veal, fish, rice food and wheat food) involved with the metabolic processes. The contributions of the principal fluorophores can be extracted from the native fluorescence spectra using a Nonnegative Constraint Blind Source Separation method. The other methods (e.g. Nonnegative Matrix Factorization (NMF)) may generate approximately similar results. The advantages of the MCR-ALS include: (1) the recovery of the spectral data and the concentrations of the principle fluorophores having positive values, and it is natural to use nonnegative constraints; and (2) since the hidden constituents in a mixed environment such as biological tissue may show different spectra other than pure principle fluorophores because of the complex surroundings, the spectra extracted by MCR-ALS can find the desired spectral signals in a mixed environment.

The results show that, with time, the emission intensity at about 450 nm (e.g. 440-460 nm) from NADH in food stored at 24° C. increases much faster than food stored at 4° C. Without wishing to be bound to any particular theory, this may be due to the catabolism of multiplying microorganisms, which is accompanied the generation of NADH. Other kinds of food such as beef, veal, fish, wheat food (e.g. bread) and rice were also investigated. Increased content of NADH over time was also observed in these other foods.

The illumination light from a light source provides the desired specific excitation wavelength. Examples of suitable light sources include laser diodes, white lamps and light emitting diodes (LEDs). In one embodiment, a filter is proximate the sample to ensure the desired wavelengths are received. In another embodiment, a filter is proximate the light source to ensure the spectral excitation wavelength is provided. The system may include additional optical components such as lasers or light emitting diodes (LEDs) with a selective wavelength, optical components (band pass filters, pass long filters and optical fibers), probe, optical detectors (compact CCD spectrometer and fiber spectrometer).

Such specific excitation wavelengths are selected to excite one or more of the principle fluorophores (collagen, NADH and flavin). In one embodiment, the specific excitation wavelength is centered at 340 nm and has a bandwidth of 40 nm (i.e. from 320 nm to 360 nm). In another embodiment, the specific excitation wavelength is centered at 380 nm and has a bandwidth of 40 nm (i.e. from 360 nm to 400 nm).

In response to the specific excitation wavelength, the principle fluorophores return a spectral signature that is characteristic of the specific fluorophore. Since at least one of the principle fluorophores, NADH, increases in concentration as microorganisms multiply, it is believed the returned spectral signal of NADH can function as a fingerprint for monitoring food spoilage.

Referring now to FIG. 1A, FIG. 1B, FIG. 1C and FIG. 1D, the average fluorescence spectral profiles with standard deviation error bars at key wavelengths for pork meat stored at 24° C. (solid-line) and 4° C. (dash line) are shown. The spectra were obtained by first exciting the sample at 340 nm and then observing the emission spectra from 350 nm to 600 nm. The emission spectra of the pork meat was measured at time intervals of 0, 1, 2, 3, 4, 5, 6, 7, 24, 31, 48, 55, 72 and 79 hours. Each spectral profile was normalized to a unit value of 1 (i.e., the sum of squares of the data elements in each emission spectra was set as 1).

Figure 1A:
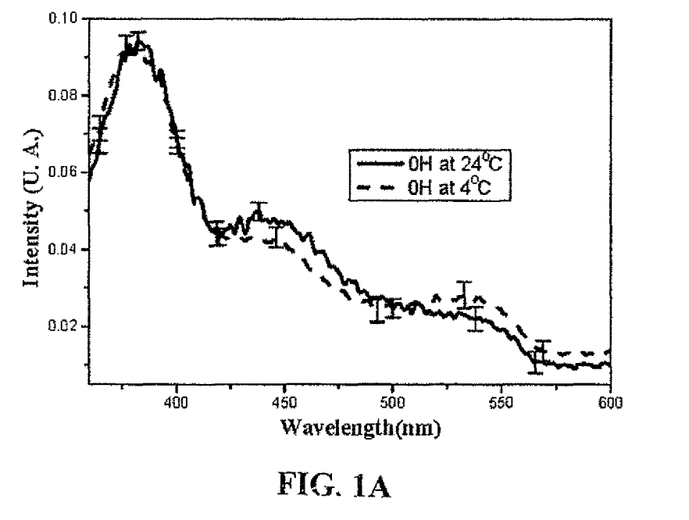
FIG. 1A, FIG. 1B, FIG. 1C and FIG. 1D are fluorescence spectra of two samples of pork meat, stored under different conditions, measured at different times.
Figure 1B:
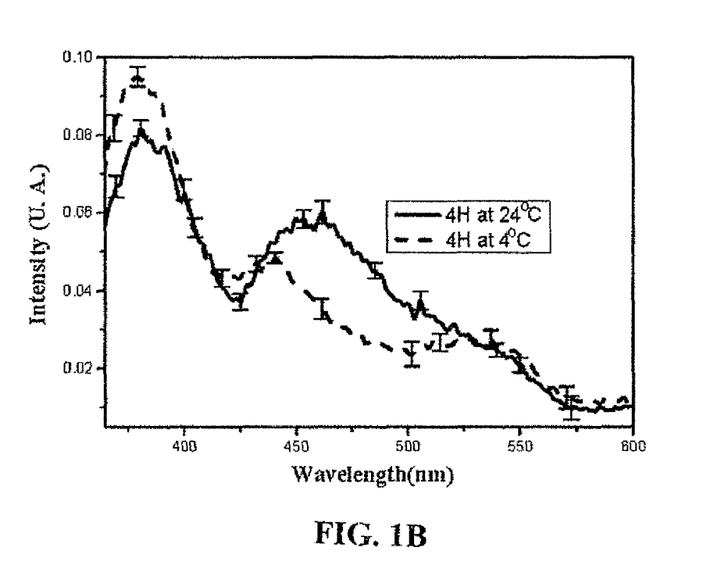
Figure 1C:
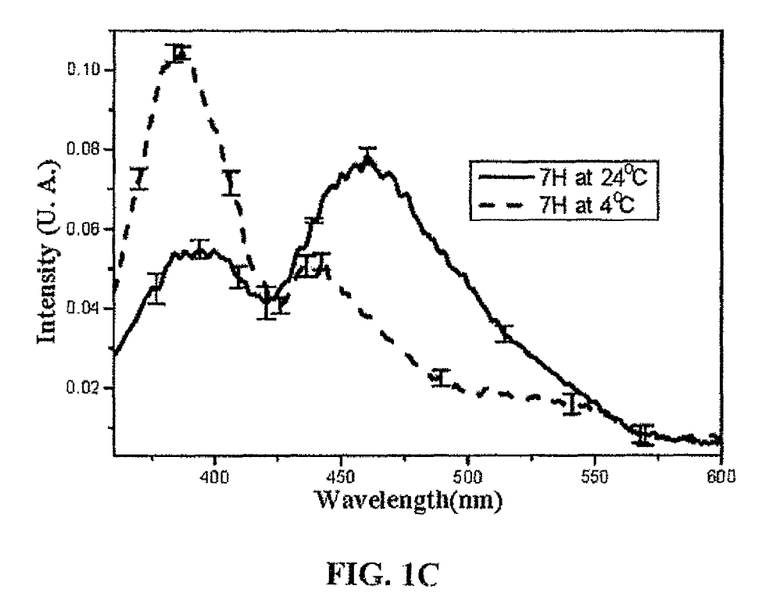
Figure 1D:
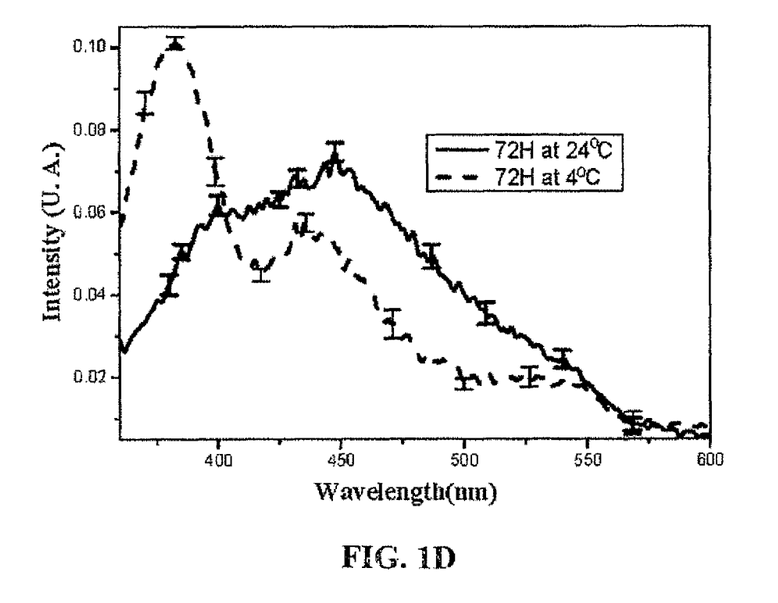

As shown in FIG. 1A the spectra at time 0 in both refrigerated and room temperature conditions has approximately the same profile with a main emission peak at about 400 nm (e.g. 380-410 nm), shoulder peaks at about 450 nm (e.g. 440-460 nm) and about 530 nm. As shown in FIGS. 1A to 1D as time elapsed, the spectral profiles of the pork meat stored under a condition of 2-4° C. showed little alteration. In contrast, the pork meat at room temperature changed significantly. The major change indicated by the solid curves in FIGS. 1A to 1D is that the shoulder peak at about 450 nm increases in intensity dramatically. These spectra show the fluorescent spectra can reveal the differences in fluorophore compositions under two different storage conditions and these spectra correlate to food spoilage. For example, by evaluating the fluorescence spectra of pork and comparing the spectra to a predetermined standard for pork, it is now possible to determine whether or not the sample had been properly stored.

For the detection of the spoilage of meat using tissue native fluorescence, it is useful to understand the contribution of each fluorophore to the native fluorescence spectra.

Figure 2A:
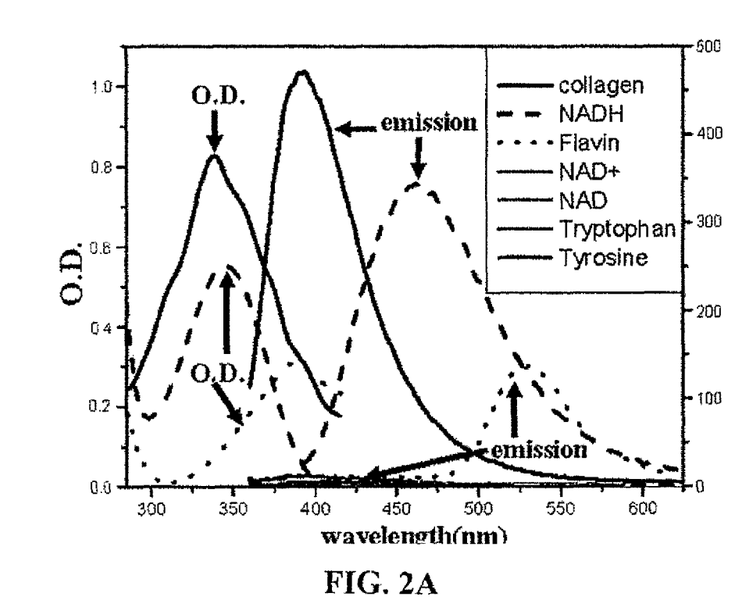

Referring now to the data in FIG. 2A, absorption and emission (excitation at 340 nm) spectra are shown for collagen, NADH, flavin and several other fluorophones (NAD+, NAD, tryptophan, tyrosine) each of which is at a concentration of about 0.75 mg per cubic centimeter. It can be seen from FIG. 2A that the absorption peaks of collagen (339 nm) and NADH (340 nm) are both about 340 nm. The major absorption peak of flavin is about 375 nm, but there is a minor absorption peak at 340 nm. Therefore, it can be understood that the fluorescence profiles of muscle foods excited by 340 nm are mainly contributed from collagen, NADH and flavin. As shown in FIG. 2A, the other fluorophores (NAD+. NAD, tryptophan, tyrosine) are non-responsive to an excitation wavelength of 340 nm. An excitation wavelength of about 340 nm is therefore anticipated to selectively excite collagen, NADH and flavin while not exciting the other fluorophores in the sample. In response to the excitation wavelength, an emission spectra is produced that is characteristic of the specific fluorophore. Collagen produces an emission peak centered at about 400 nm (e.g. 380-410 nm), NADH produces an emission peak centered at about 450 nm (e.g. 440-460 nm), while flavin produces an emission peak centered at about 530.

Figure 2B:
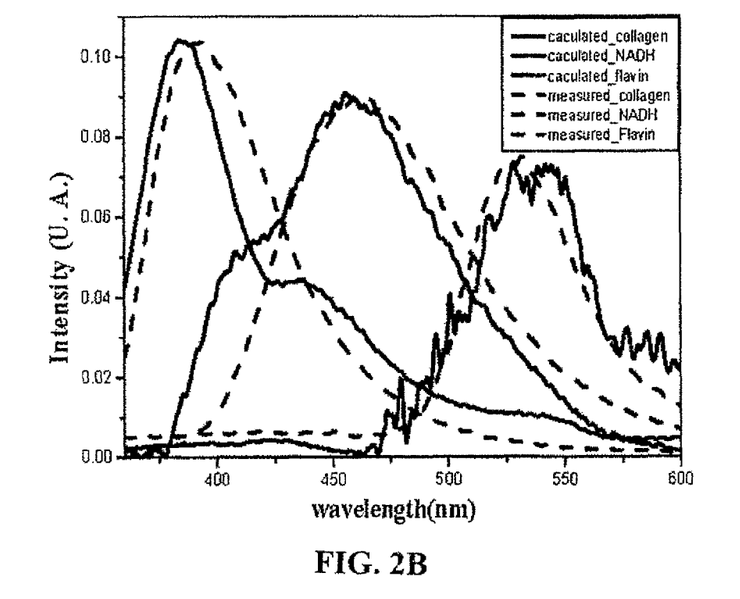
FIG. 2B is a comparison of MCR-ALS-calculated spectra and the measured spectra of collagen, NADH and flavin.

Referring now to FIG. 2B, the emission spectra was extracted from a native fluorescence spectra using a Multivariate Curve Resolution with Alternating Least-Squares (MCR-ALS) calculation. MCR-ALS was applied to extract the relative concentration changes of these three fluorophores by treating collagen, NADH and flavin as principal fluorophores for the fluorescence spectra with 340 nm excitation. Using the wavelengths in this range, one can study the relationship between relative concentration changes of principal fluorophores of food spoilage at different times under two different storing conditions by calculating the basis spectrum and contribution of each component spectrum to the total fluorescence spectra of the muscle foods calculated using MCR-ALS.

Referring again to FIG. 2B the extracted emission spectra of the principal fluorophores are shown as solid lines. The measured individual spectra of collagen, NADH and flavin were plotted as dash lines as internal references. The minor difference between the extracted and measured spectra of each component was mainly arisen from different measuremental environment, such as viscosity, pH value of solvent medium, concentration of the fluorophore and distortions caused by cell scattering and absorption. The two groups of spectra show reasonable agreement with each corresponding counterpart, which demonstrates that MCR-ALS model accounts for the major spectroscopic feature observed. The leading three principal fluorophores of collagen, NADH and flavin were accounted as 99.5% of the total variance. This means adding an extra component (a fourth principle component) will not significantly alter the variance that is based on these three principle components. It follows that the spectra of collagen, NADH and flavin provide a predetermined standard against which measured data can be compared. For example, the relative concentration of collagen can be determined by exciting at a wavelength of about 340 nm and observing the returned spectra at a wavelength of about 400 nm. Likewise, for example, the relative concentration of NADH can be determined by exciting at a wavelength of about 340 nm and observing the returned spectra at a wavelength of about 450 nm (e.g. 440-460 nm).

Figure 3A:
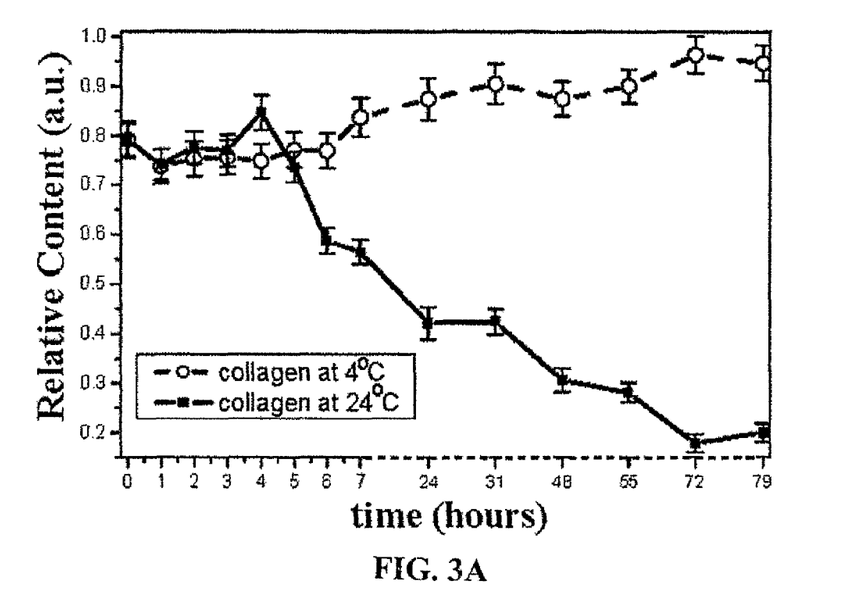
FIG. 3A and FIG. 3B show MCR-ALS-calculated content changes as a function of measuring time for collagen (FIG. 3A) and NADH (FIG. 3B)
Figure 3B:
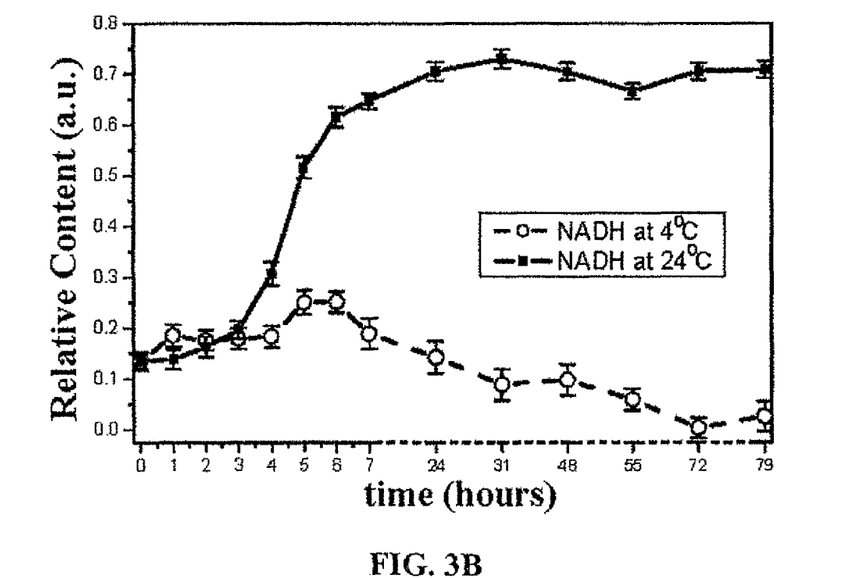

FIG. 3A and FIG. 3B show the average relative concentrations of a sample with standard deviation error bars of collagen (FIG. 3A) and NADH (FIG. 3B) at 20-24° C. (solid line) and 2-4° C. (dashed line) at time intervals of 0, 1, 2, 3, 4, 5, 6, 7, 24, 31, 48, 55, 72 and 79 hours. The NADH concentration increases as collagen concentration decreases at room temperature with time. To characterize the relative concentration changes of fluorophores, the relative concentrations of NADH and collagen in tissues at 2-4° C. (in refrigerator) and 20-24° C. (in room temperature) were extracted at different elapsed times using MCR-ALS. The relative concentrations under two different conditions at time 0 are normalized to have the same value since it was assumed that conditions of the samples are initially equal.

The significant features of FIG. 3A and FIG. 3B include: (1) in the initial three hours, the concentration of both NADH and collagen vary slightly; (2) dramatic increase in the relative concentration of NADH at 20-24° C. happens at the fourth hour while that of NADH at 2-4° C. still has small fluctuations; and (3) after 24 hours, the concentration of NADH at 2-4° C. shows a slight decrease while NADH. at 20-24° C. still has small fluctuations. The concentration change of NADH exhibited in FIG. 3B reflects the microbial spoilage of foods involved with the metabolic processes. The fresh foods consist of roughly 75% water, 19% protein, and the rest substances including intramuscular fat, carbohydrates and other soluble non-protein.

Collagen serves as a major component of the endomysium of muscle foods, constituting 2% of muscle tissue, and up to 6% >>of strong, tendinous muscles. NADH is present in every cell of animals and plants and meat contains about 50 mg per kilogram. Since 340 nm is selected as the excitation wavelength, which is close to the absorption peaks of collagen and NADH, the emission signals contributed from collagen and NADH can be considered and detected as the principal signal at beginning several hours. During processing, the meat may be infected by additional microorganisms that multiply at room temperature. The microbial metabolism is increased dramatically with the number of spoilage flora developed in a geometric ratio. Usually, microorganisms grow well when in the temperature of 5° C.-65° C. with a good supply of nutrients. While proliferation of microorganisms occurs under room temperature, they need energy to maintain metabolism by oxidation of reduced carbon compounds during aerobic and/or nitrate respiration. In either process, NADH will be generated. The concentration of NADH suggests metabolic and/or growth rate of the multiplying microorganisms.

It is well known that the typical microorganism growth curve exhibits the following growth dynamics: lag phase (initial time adjusting to the new medium), exponential phase (time for bacteria to divide regularly by the process of binary fission), stationary phase (time to stop dividing when growth becomes limited because of less nutrition, water and temperature e.g.), and finally death phase (time to show loss of viability because of exhausting the nutrition e.g.). The time intervals for the four phases depends on different kinds of environments/media (in our case: different types of meat) and bacteria. Usually, bacterial growth rates are defined by the bacterium's generation time, which is defined as the time required for bacterial mass to double. Generation times for bacteria vary from about tens of minutes to a day or more. For example, generation time of *E. coli* bacteria in laboratory, some strains of which (*E.coli* 0157) causing severe food poisoning for kidney failures is 15-20 minutes, but in the intestinal tract, the coliform's generation time is estimated to be 12-24 hours. Since NADH plays an important role in the metabolism of the microorganisms through aerobic and/or nitrate respiration, it is reasonable to conclude that the evolving trend of NADH content under room temperature somehow corresponds to growth dynamics of certain types of bacteria in the meat media. This can be verified by the control data obtained from meat samples stored in a refrigerator. Since bacteria can only divide over 5° C., refrigeration at 2-4° C. prevents bacteria multiplying so NADH content shows tiny fluctuation for the first day. The slow decay can be observed after 24 hours. This can be understood that the survival rate of bacteria in Stuart's transport medium was reported as 81.9% at 22° C. In a refrigerator, bacteria stop multiplying and die slowly. Without wishing to be bound to any particular theory, this may explain the features shown by the curve of NADH under 2-4° C. in FIG. 3B.

Figure 4A:
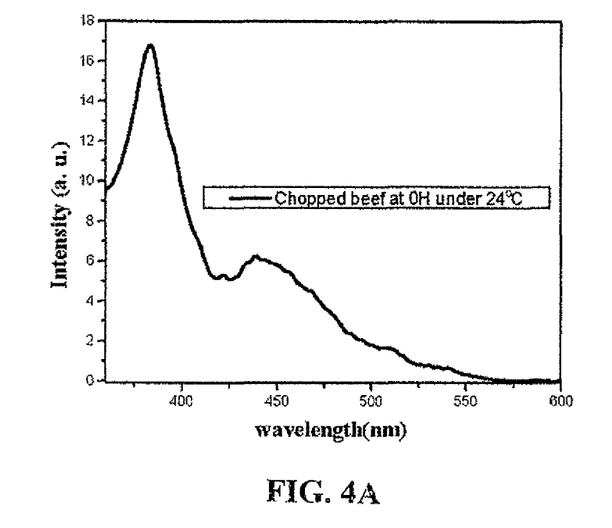
FIG. 4A and FIG. 4B are fluorescence spectra of chopped beef meat stored at room temperature and measured at hour 0 (FIG. 4A), and hour 2 (FIG. 4B)
Figure 4B:
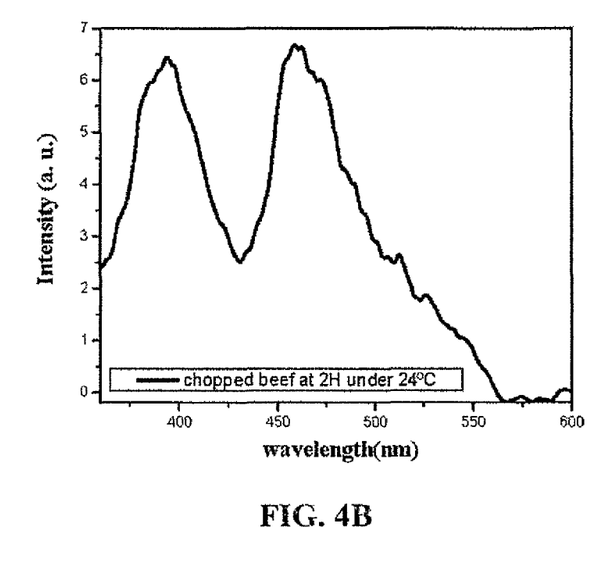

FIGS. 4A and 4B show the fluorescence spectra of chopped beef meat stored at 20-24° C. (room temperature) excited with 340 nm and measured at times of hour 0 (FIG. 4A) and hour 2 (FIG. 4B). The features of FIGS. 4A and 4B reflect results similar to those observed in FIGS. 1A to 1D: relative concentration of NADH increases for meat stored at room temperature. As shown in FIG. 4A, the spectra shows a main emission peak at about 400 nm for collagen with shoulder peaks at about 450 nm (e.g.440-460 nm) for NADH at hour 0. At hour 2 the shoulder peak at about 450 nm increases in intensity dramatically relative to the corresponding intensity of the peak at about 400 nm for collagen. Compared with pork meat at hour 4 shown in FIG. 1B, the NADH peak for chopped meat rises faster than that of pork meat. This can be understood that, on whole, meat bacteria grow only on the contaminated surface, where they dwell on the exudates, i.e. the glucose and amino acid rich liquid which leaks from damaged cells and blood vessels. If the meat is minced this surface and exudates increase enormously which leads to much higher microbial activity and growth in the inner anaerobic parts of the minced meat. In one embodiment, the relative intensities (e.g. the ratio) of two peaks are analyzed to determine whether or not the food has spoiled. For example, in one embodiment, the ratio of the NADH peak (about 450 nm) to the collagen peak (about 400 nm) is analyzed. For example, when the NADH to collagen signal intensity ratio is less than 0.6, the food may be determined to be not spoiled. When the ratio is greater than 0.6 to 0.7, the food may be determined to be borderline. When the ratio is greater than 0.7, the food may be determined to be spoiled.

Figure 5A:
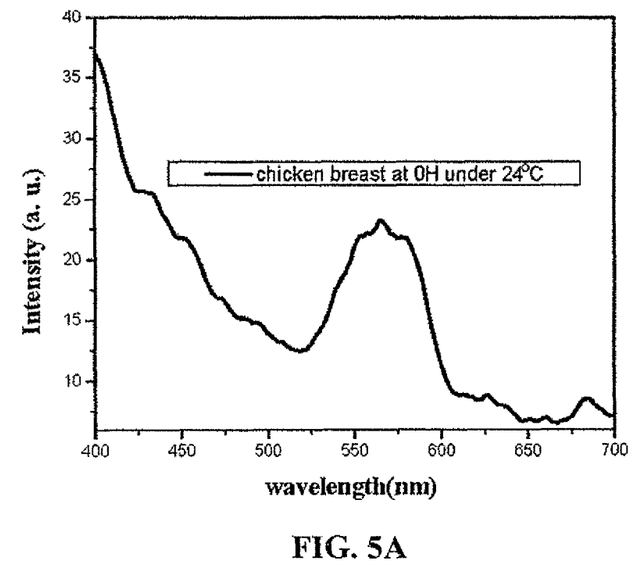
FIG. 5A and FIG. 5B are fluorescence spectra of chicken breast stored at room temperature and measured at hour 0 (FIG. 5A), and hour 12 (FIG. 5B)
Figure 5B:
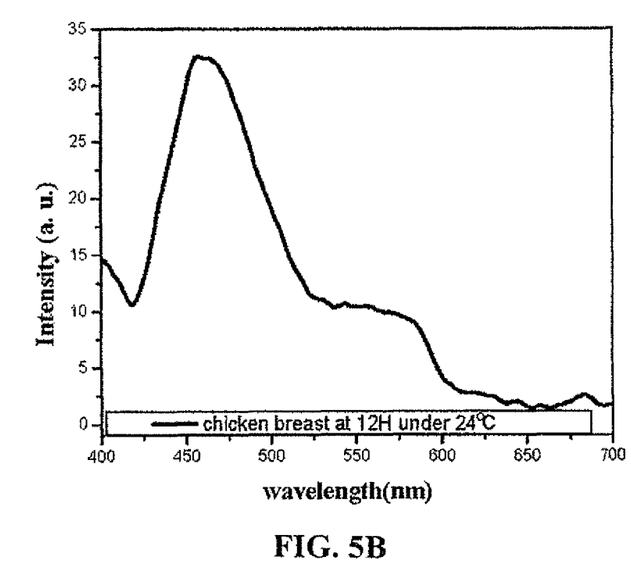

Referring now to FIGS. 5A and 5B, the fluorescence spectra of chicken breast is shown. The chicken breast is stored at 20-24° C. (room temperature) excited with 380 nm and measured at hour 0 (FIG. 5A) and hour 12 (FIG. 5B). The features of FIGS. 5A and 5B show no obvious peak at about 450 nm for NADH at hour 0, but an obvious peak is observed at about 530 nm for flavin. With time, the intensity of the NADH peak increases and overtakes the flavin intensity. FIGS. 5A and 5B indicates that emission spectra of foodstuff excited by about 380 nm can also be used to detect the spoilage degree of meat by monitoring the changes of NADH caused by bacteria.

Figure 6A:
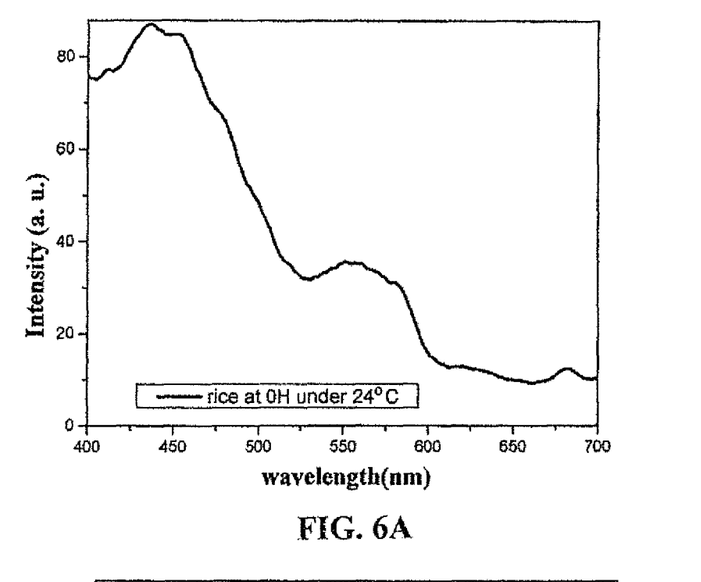
Figure 6B:
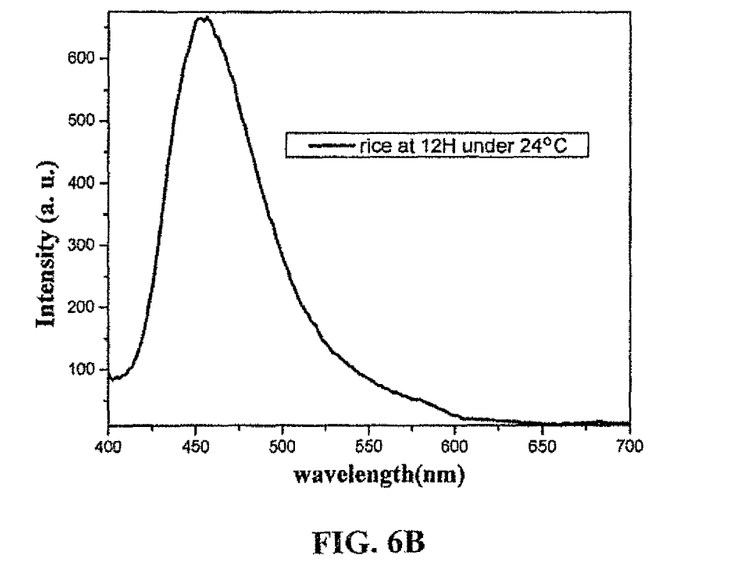
Figure 6C:
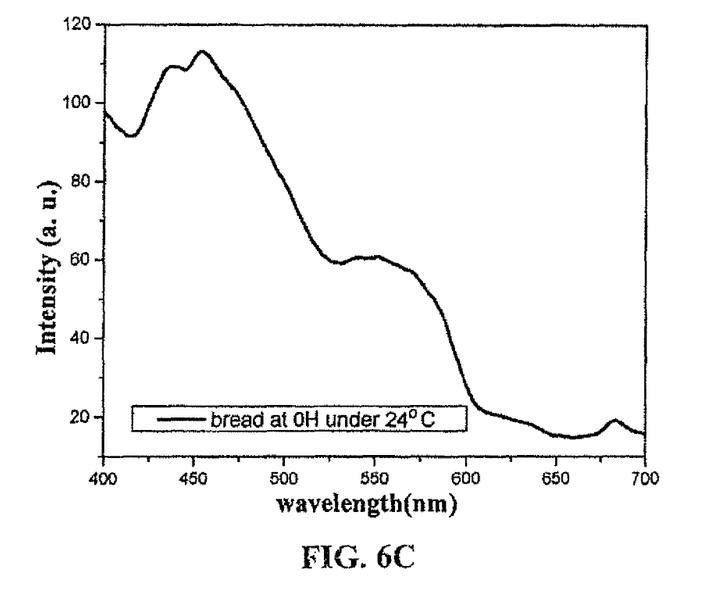
FIG. 6C and 6D are fluorescence spectra of Chinese bread stored at room temperature measured at hour 0 (FIG. 6C) and hour 12 (FIG. 6D)
Figure 6D:
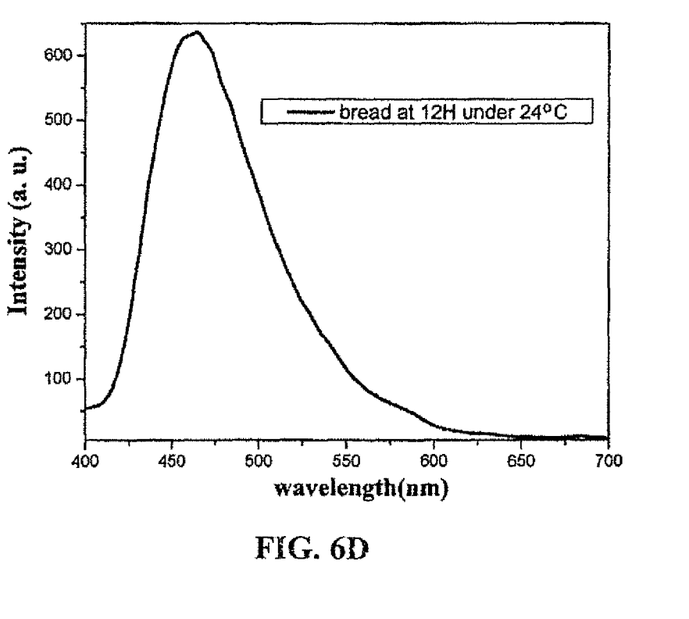

FIG. 6A to 6D shows the fluorescence spectra of cooked grain stored at 20-24° C. (room temperature) excited with 380 nm and measured at hour 0 (FIG. 6A), and hour 12 (FIG. 6B) for white rice; hour 0 (FIG. 6C), and hour 12 (FIG. 6D) for Chinese bread. The features of FIG. 6A include a peak at about 450 nm peak for NADH that is observed at hour 0, and an obvious shoulder peak is observed at about 530 nm for flavin. With time elapse, the peak of NADH overtakes the flavin peak (FIG. 6B and FIG. 6D).

No peak at about 530 nm for flavin is observed after 12 hours. FIGS. 6A to 6D indicates that emission spectra of food excited by about 380 nm can be extended to detect the spoilage degree of grain by monitoring the changes of NADH caused by bacteria.

In another embodiment, the methods and system described herein provide for the real-time monitoring in vivo of metabolic and/or growth rate of multiplying microorganisms outside of the realm of food spoilage.

The method may be embodied in a relatively small and portable device. In one embodiment, the device may take the form of a handheld device in the general shape of a pen, a watch or a cellular telephone. The device includes a means for emitting an excitation wave with a first wavelength (e.g. 340 nm and/or 380 nm). The means for emitting may be a suitable light source, including a light emitting diode (LED), monochromatic light source, or a light source with filters to select for the first wavelength. The device further includes a means for detecting the emission spectra that is returned by the food upon its exposure to the first wavelength. The means for detecting may include a suitable photosensor, including a charge-coupled device (CCD). In one embodiment, the means for detecting is sensitive only to a second wavelength (e.g. 400 nm, 450 nm and/or 530 nm). The device may further comprise a microprocessor for processing signals from the means for detecting. In one embodiment, the means for detecting receives a relatively broadband signal and the microprocessor subsequently limits the analyze to only the second wavelength. In one embodiment, spoilage is detected by emitting the first wavelength and imaging the resulting second wavelengths using a CCD camera in a cellular telephone. The device may further comprise a display such as a numeric display (e.g. displaying a value between 0.00 and 1.00), a graphic display (imaging the food); a binary display (red light/green light to show spoilage) and the like such as an audio output that issues an audio alert (sound or voice) that reflects the spoilage, if any, in a food product.

Figure 7:
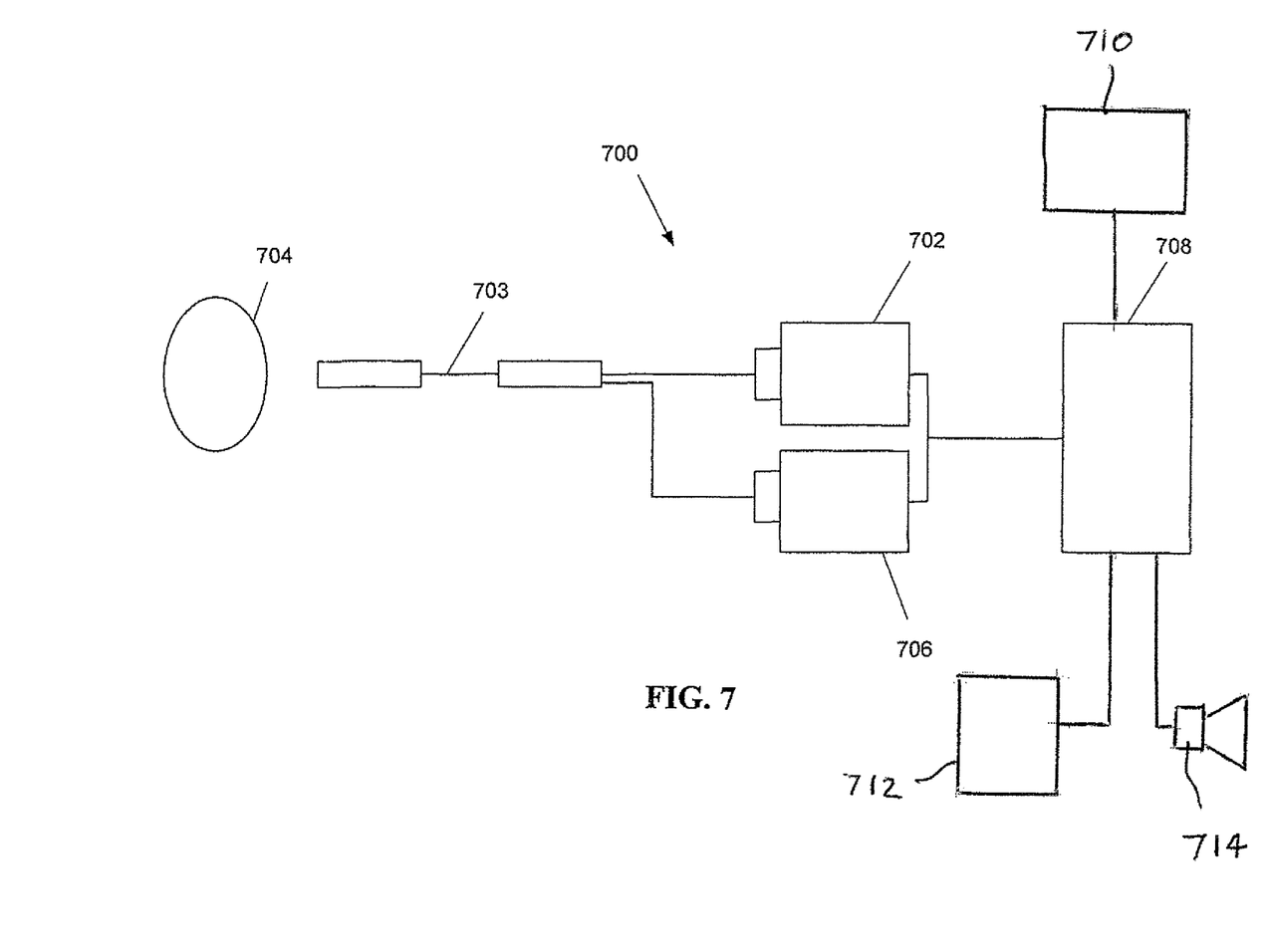
FIG. 7 depicts an exemplary system for detecting the degree of spoilage of a food sample.

Referring to FIG. 7, a system 700 for detecting the degree of spoilage of a food sample is depicted. The system 700 comprises a light source 702 that emits excitation waves of a first wavelength (e.g. about 340 nm). An optical fiber probe 703 guides the excitation wave to a food sample 704. The resulting emission spectra is returned, in the form of backscattered light, to detector 706. In the exemplary embodiment of FIG. 7 the emission spectra is returned along the optical fiber probe 703. Detector 706 detects light at one or more second wavelength (e.g. about 400 nm, about 450 nm, and/or about 530 nm). In one embodiment, light is detected at second wavelengths of about 400 nm and about 450 nm. The emission spectra is analyzed by microprocessor 708. In one embodiment, the analysis comprises the step of determining the ratio of the intensity at about 450 nm to the intensity at about 400 nm. A determination is then made based on whether or not the food sample is spoiled beyond a predetermined threshold. For example, a predetermined threshold may be a 450 nm to 400 nm intensity ratio of 0.5. A user of the system 700 may determine a given food sample has a 450:400 nm ratio of 0.3 and deem the food is fresh. A user may determine a 450:400 nm ratio for a different food sample to be 0.5 and deem the food sufficiently fresh but subsequently cook the food longer. Similarly, a user may determine the 450:400 nm ratio of 0.8 and deem the food is spoiled. These results may be shown on a display, monitor or screen 712. The microprocessor may be programmed to output the threshold and actual measured intensity values, for pre-programmed food products, as well as selective indicators (e.g. green/red; "fresh"! "spoiled"; "can use"/ "do not use", and the like) or intensity levels or ratios. An audio transducer, shown as a speaker 714, can also be used to communicate the status of a selected food product, including using audible (e.g. synthesized voice) announcements of the status of the condition of a food product or selected sounds (e.g. buzzer) when food is determined to be spoiled based on predetermined or pre-established intensity levels or ratios of values.

Figure 8:
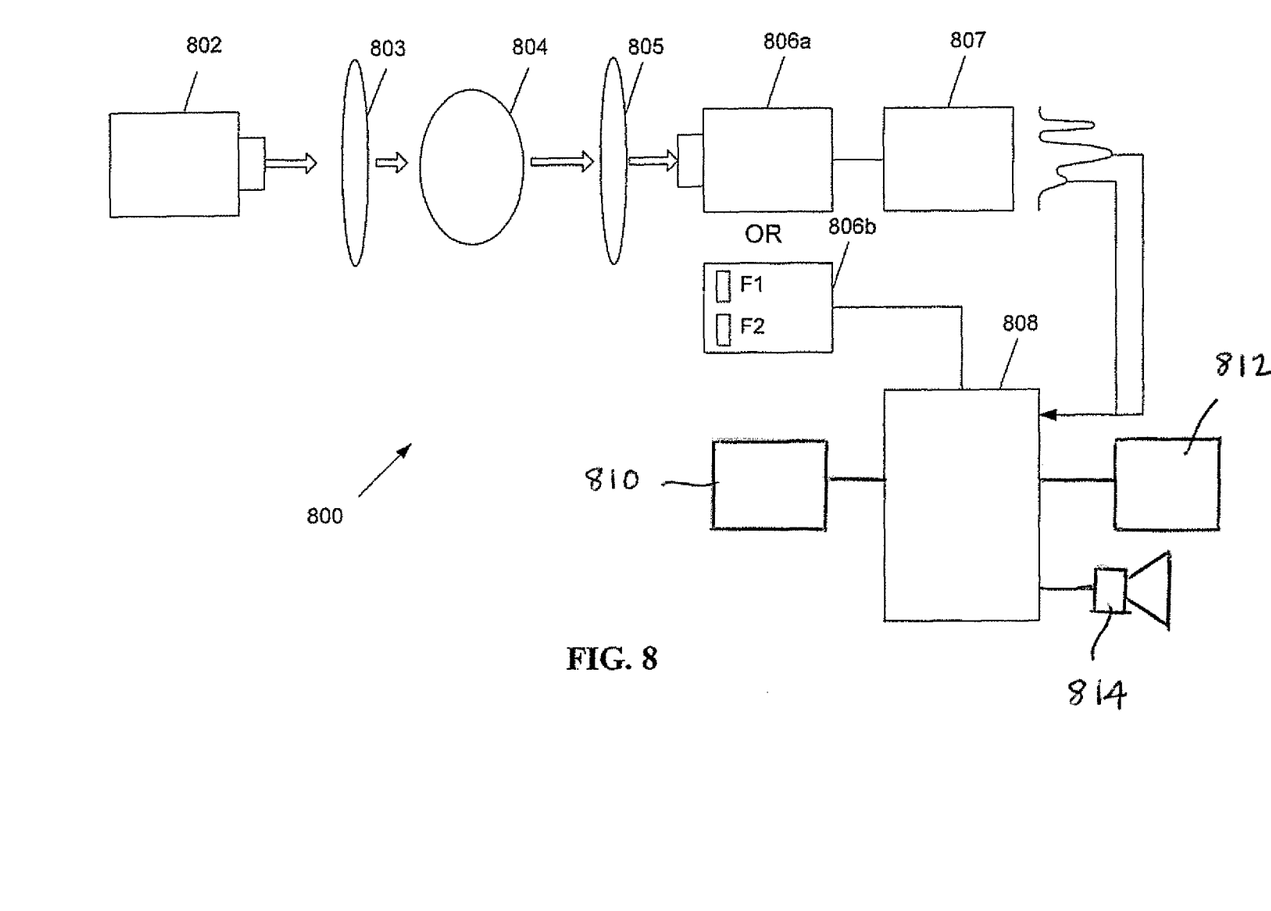
FIG. 8 depicts another exemplary system for detecting the degree of spoilage of a food sample.

FIG. 8 depicts a system 800 for detecting the degree of spoilage of a food sample. The system 800 comprises a light source 802 that emits excitation waves of a first wavelength (e.g. about 340 nm). The excitation waves may be processed through first optical elements 803. Examples of first optical elements include lenses, fiber optics, filters and other light manipulating elements. In one embodiment, the first optical element is a filter that selects for a first wavelength. The excitation wave then contacts food sample 804. The resulting emission spectra is transmitted to a detector, such as detector 806a or detector 806b. In one embodiment, the emission spectra is transmitted through second optical elements 805. In one such embodiment, the second optical element is a filter that selects for one or more second wavelengths. Detector 806a is a spectrometer that processes the emission spectra into a fluorescent spectrum. The fluorescent spectrum is provided to an imaging sensor 807. The imaging sensor 807 may be, for example a CCD photosensor or a complementary metal oxide semiconductor (CMOS) photosensor. The intensities of select second wavelengths are then analyzed by a microprocessor 808 for determination of the degree of spoilage of the food sample 804. In one such embodiment, one can image the spoilage using the CCD camera in a cellular telephone. Alternatively, the detector may be a narrowband detector 806b which is sensitive to only the desired second wavelengths (F1 and F2). For example, the narrowband detector 806 may be sensitive to second wavelengths of about 400 nm and about 450 nm. The intensities of these select second wavelengths are then analyzed by the microprocessor 808 for determination of the degree of spoilage of the food sample 804.

Figure 9:
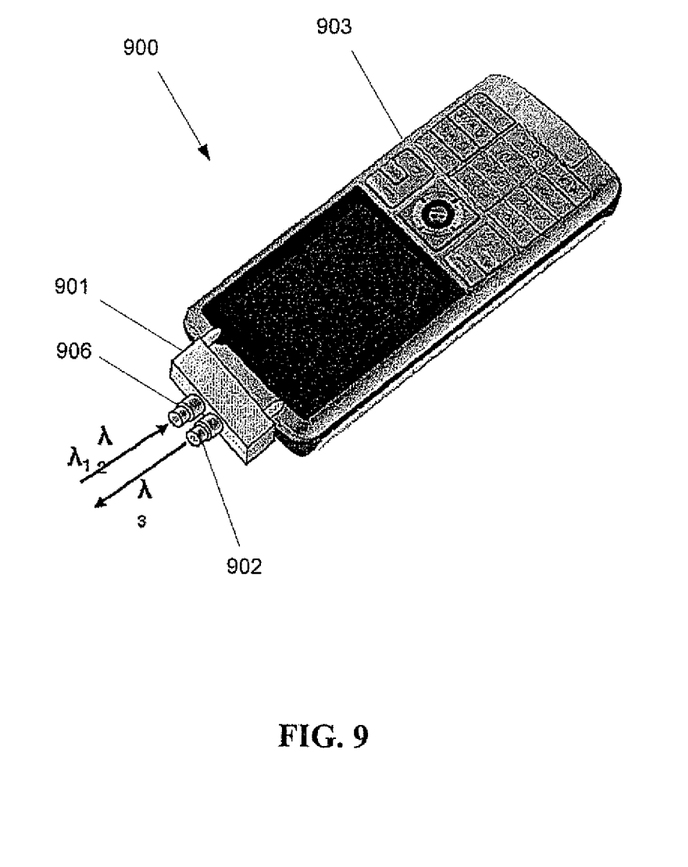
FIG. 9 is a depiction of an exemplary portable device for detecting the degree of spoilage of a food sample.

FIG. 9 is a depiction of an exemplary device 900 for detecting the degree of spoilage of a food sample. The device comprises a microprocessor such as a microprocessor of cellular telephone 903. An attachment 901 is connected to the cellular telephone 903 to provide a wired connection. In another embodiment, the attachment 901 is in wireless communication with the cellular telephone 903. The attachment 901 comprises a light source 902 that emits excitation waves of a first wavelength (e.g. about 340 nm). The attachment 901 further comprises a detector 906 for detecting light at one or more second wavelength (e.g. about 400 nm, about 450 nm, and/or about 530 nm). In one embodiment, light is detected at second wavelengths of about 400 nm and about 450 nm.

Figure 10:
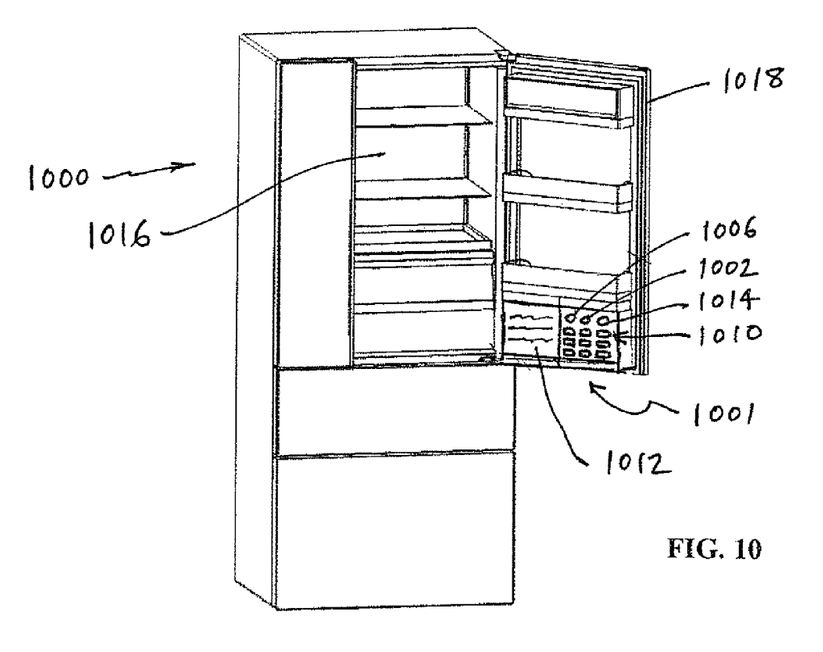
FIG. 10 illustrates a cooling or refrigeration unit incorporating a food spoilage detection device in accordance with the invention.

As suggested, the method of the invention may be implemented by using a small portable/handheld unit such as the cell phone attachment 901 shown in FIG. 9, a pen, watch or other portable item. However, a device in accordance with the invention for implementing the method of the invention may also be incorporated into larger food processing, storage or refrigeration systems or facilities including residential, commercial or industrial food storage or refrigeration units. Referring to FIG. 10, a residential refrigerator 1000 is illustrated, by way of example, that incorporates a spoilage detection device 1001 according to the invention. The refrigerator 1000 includes food compartments 1016 for storage of food items and a door 1018. The device 1001 can include components similar to those shown in FIGS. 7-9, including an input device 1010 (shown as a keypad), a display 1012, a light source 1002, a light sensor or detector 1006 and a speaker or buzzer 1014. With the door open, a selected food item can be removed from the refrigerator and positioned in front of the light source 1002. The emission spectra is received by the detector 1006 so that a microprocessor 708/908 (FIGS. 7, 8) can establish the status of the food product and a suitable output issued to the display 1012 and/or audio transducer 1014.

Figure 11:
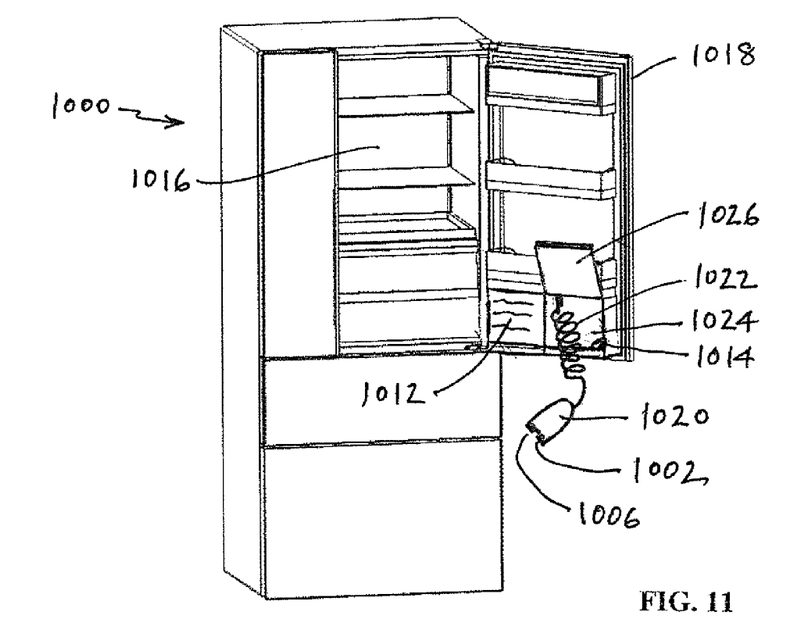
FIG. 11 is similar to FIG. 10 and illustrates a modified food spoilage detection device in accordance with the invention.

Referring to FIG. 11 a modified embodiment is shown in which the food spoilage detection device 1001' includes a light source 1002 and a detector 1006 mounted on a support member 1020 shaped and dimensioned to be easily gripped by a user. The support member 1020 is connected by means of an optical fiber 1022, shown coiled, to enable a user to move and position the support member 1020 proximate to a food item before and after it is removed from the refrigerator. The optical fiber 1022 is made sufficiently long and flexible so that the support member 1020 can be extended to position the support member not only in juxtaposition with a food item removed from the refrigerator but in juxtaposition against surfaces in the interior walls or shelves in the refrigerator to detect the presence of activity by microorganisms on the interior refrigerator surfaces. The door 1018 advantageously has a compartment 1024 for safely receiving the coiled optical fiber cable 1022 and support member 1020 when not in use. When so stored, a door 1018 can selectively provide access to the compartment 1024 while protecting the optical fiber 1022 and the optical components connected thereto.

While the invention has been described with reference to certain embodiments, it will be understood by those skilled in the art that various changes may be made and equivalents may be substituted for elements thereof to adapt to particular situations without departing from the scope of the disclosure. Therefore, it is intended that the claims not be limited to the particular embodiments disclosed, but that the claims will include all embodiments falling within the scope and spirit of the appended claims.

What is claimed is:

1. A method for detecting the degree of spoilage of food, the method comprising the steps of:
   exposing a sample of food to an excitation wave having a first wavelength of about 340 nm or about 380 nm within a first range of wavelengths, wherein the excitation wave has a bandwidth of 40 nm or less;
   permitting the excitation wave to interact with the food sample and return an emission spectra;
   detecting the emission spectra with a detector;
   establishing a predetermined threshold value of at least one of NADH, collagen and flavin which defines when a food sample is or is not spoiled;
   analyzing the emission spectra at a second wavelength of at least one of about 400 nm, about 450 nm or about 530 nm within a second range of [380 nm to 600 nm] wavelengths to provide a measured value of said emission spectra indicative of concentrations of NADH, collagen and flavin, respectively, and a degree of spoilage of the food sample, said first range of wavelengths being below said second range of wavelengths; and
   determining whether or not the food sample is spoiled by comparing said measured value to said predetermined threshold value of said at least one of NADH, collagen and flavin.

2. The method as recited in claim 1, wherein said second wavelength is between about 440 nm and 460 nm.

3. The method as recited in claim 1, the method further comprising the step of monitoring the food sample over time by waiting a period of time and thereafter:
   repeating the step of exposing the food sample to the excitation wave;
   repeating the step of permitting the excitation wave to interact;
   repeating the step of detecting the emission spectra; and
   repeating the step of analyzing the emission spectra at a second wavelength.

4. A method as recited in claim 1, wherein said emission spectra is analyzed at a second wavelength of about 400 nm to provide a first measured value and at a third wavelength of about 450 nm to provide a second measured value, a ratio of said first and second measured values being a ratio indicative of a degree of spoilage of the food sample; and
   determining whether or not the food sample is spoiled beyond said predetermined threshold value by comparing the ratio of said first and second measured values to said predetermined threshold value.

5. The method as recited in claim 4, wherein said predetermined threshold value is selected to be a ratio of said second measured value to said first measured value.

6. The method as recited in claim 4, wherein the food sample is selected from the group consisting of pork, chicken, beef, fish, rice food and wheat food.

7. The method as recited in claim 5, wherein said ratio is selected to indicate food spoilage when said ratio exceeds 0.6.

8. A device for detecting the degree of spoilage of food, the device comprising:
   a light source for emitting an excitation wave and exposing a sample of food with a first wavelength selected from the group consisting of 340 nm, 380 nm within a first range of wavelengths nm and combinations thereof;

a detector for detecting an emission spectra that is returned by the sample of food upon its food's exposure to said first wavelength;

a microprocessor programmed for processing signals from said detector at second wavelength of at least one of about 400 nm, about 450 nm or about 530 nm within a second range of wavelengths to provide a measured value indicating concentrations of NADH, collagen and flavin, respectively, and of a degree of spoilage of the food sample and determining whether or not the food sample is spoiled beyond a predetermined threshold value by comparing said measured value to said predetermined threshold value of said at least one of NADH, collagen and flavin, said first range of wavelengths being below said second ranged of wavelengths; and an output device for receiving output from said microprocessor.

9. The device of claim 8, wherein said output device is a visual display.

10. The device of claim 8, further comprising a filter disposed proximate said detector for filtering the emission spectra such that a second wavelength of light contacts said detector, the second wavelength being selected from the group consisting of 400 nm, 450 nm and 530 nm.

11. The device of claim 8, wherein the microprocessor and the display are part of a cellular telephone and said light source and said detector are attached to the cellular telephone.

12. The device of claim 8, wherein the light source comprises a light emitting diode.

13. The device of claim 8, wherein the detector comprises a charge-coupled device (CCD).

14. A device of claim 8, wherein said device is incorporated into a food cooling unit.

15. A device of claim 8, further comprising an audio output device for generating an audio signal generated by said microprocessor to audibly indicate the freshness condition of the food when detected by the food spoilage device.

16. A method for detecting the degree of spoilage of food, the method comprising the steps of:

exposing a sample of food to an excitation wave having a first wavelength within the range of 340-380 nm within a first range of wavelengths wherein the excitation wave has a bandwidth of 40 nm or less;

permitting the excitation wave to interact with the food sample and return an emission spectra;

detecting the emission spectra with a detector within the range of 380-600 nm;

establishing a predetermined threshold value of at least one of NADH, collagen and flavin which defines when a food sample is or is not spoiled;

analyzing the emission spectra at a second wavelength of at least one of about 400 nm, about 450 nm or about 530 nm within a second range of wavelengths to provide a measured value at said emission spectra indicative of a degree of spoilage of concentrations of NADH, collagen and flavin, respectively, and the food sample, said first range of wavelengths being below said second range of wavelengths; and determining whether or not the food sample is spoiled beyond said predetermined threshold by comparing said measured value to said predetermined threshold value of said at least one of NADH, collagen and flavin.

\* \* \* \* \*